(12) United States Patent
Ingelbrecht et al.

(10) Patent No.: US 7,423,184 B2
(45) Date of Patent: Sep. 9, 2008

(54) METHOD OF MAKING CARBONYL COMPOUNDS

(75) Inventors: Hugo Ingelbrecht, Antwerp (BE); Arun Kumar, Karanataka (IN); Ashok Ramakrishnan Menon, Maharashtra (IN); Pradeep Nadkarni, Karnataka (IN); Rupesh Pawar, Maharashtra (IN)

(73) Assignee: Sabic Innovative Plastics IP B.V. (NL)

( * ) Notice: Subject to any disclaimer, the term of this patent is extended or adjusted under 35 U.S.C. 154(b) by 61 days.

(21) Appl. No.: 11/214,294

(22) Filed: Aug. 29, 2005

(65) Prior Publication Data

US 2007/0049767 A1     Mar. 1, 2007

(51) Int. Cl.
*C07C 45/29* (2006.01)

(52) U.S. Cl. ............... 568/315; 568/361; 568/402; 568/431; 568/471

(58) Field of Classification Search ............... None
See application file for complete search history.

(56) References Cited

U.S. PATENT DOCUMENTS

| | | | |
|---|---|---|---|
| 2,005,645 A | 6/1935 | Bond et al. | 260/138 |
| 2,218,457 A | 10/1940 | Whinaos | 260/586 |
| 2,462,413 A | 2/1949 | Meathe | 260/603 |
| 4,900,708 A | 2/1990 | Bennett et al. | 502/340 |

FOREIGN PATENT DOCUMENTS

| JP | 2003096016 A2 | 4/2003 |
|---|---|---|
| PL | 55443 | 4/1968 |

OTHER PUBLICATIONS

Kijenski, et al. Hydrogen transfer over magnesium oxide; an alternative for hydrogenation-deydrogenation reactions, Studies in Sufrace Science and Catalysis (1988), 41 (Heterog. Catal. Fine Chem.), 231-40.
Polymer-supported oxidants for the conversion of primary alcohols to aldehydes, NovaBiochem, No. 4/00.
Valarivan , et al. Reaction of benzyl alcohol over the hydrogen storage intermetallic compound Mg2Cu. Reaction Kinetics and Catalysis Letters (1996), 59(2), 343-350.
Saadi, et al. Cu/MO (M=Mg, Ca, Sr) catalysts. Characteristics identified by reactions tests. Journal de la Societe Algerienne de Chimie (2001), 11 (2), 231-240.
Saadi, et al., Catalysts Cu/MO (M=Mg, Ca, Sr). Characterisations By Test Reactions, Journal of the Algerian Chemical Society, 2001, 11(2), pp. 231-240, Translation.

*Primary Examiner*—Sikarl A Witherspoon
(74) *Attorney, Agent, or Firm*—Cantor Colburn LLP

(57) ABSTRACT

A method of making a carbonyl compound comprises contacting a compound comprising a secondary hydroxyl group with a basic metal oxide catalyst at a temperature sufficient to maintain the compound comprising a secondary hydroxyl group in a vapor phase.

13 Claims, No Drawings

METHOD OF MAKING CARBONYL COMPOUNDS

BACKGROUND OF THE INVENTION

This disclosure relates to methods of making carbonyl compounds.

Carbonyl compounds are important in a wide range of applications, both as a final product and as an intermediate. For instance, aromatic aldehydes are widely employed as intermediates that can be reacted further and as final products in a range of areas including fragrances, insecticides, herbicides and polymers. In addition carbonyl compounds find use pharmaceuticals and additives such as light stabilizers.

Aromatic aldehydes have been produced by the dehydrogenation (oxidation) of aromatic alcohols and hydrogenation (reduction) of aromatic carboxylic acids. Most approaches require some type of catalyst and specialized reaction conditions. Frequently the catalyst, the reaction conditions, the yield, or a combination of the foregoing are not suitable for manufacture on a commercial scale.

Accordingly, a continuing need exists in the art for methods of making carbonyl compounds in a cost effective manner.

BRIEF DESCRIPTION OF THE INVENTION

The foregoing need is addressed by a method of making a carbonyl compound comprising contacting a compound comprising a secondary hydroxyl group with a basic metal oxide catalyst at a temperature sufficient to maintain the compound comprising a secondary hydroxyl group in a vapor phase.

DETAILED DESCRIPTION OF THE INVENTION

In this specification and in the claims, which follow, reference will be made to a number of terms which shall be defined to have the following meanings.

The singular forms "a," "an," and "the" include plural referents unless the context clearly dictates otherwise.

"Optional" or "optionally" means that the subsequently described event or circumstance may or may not occur, and that the description includes instances where the event occurs and instances where it does not.

"Combination" as used herein includes mixtures, copolymers, reaction products, blends, composites, and the like.

The endpoints of all ranges reciting the same characteristic are independently combinable and inclusive of the recited endpoint. Values expressed as "greater than about" or "less than about" are inclusive the stated endpoint, e.g., "greater than about 3.5" encompasses the value of 3.5.

Disclosed herein are methods of making compounds comprising a carbonyl group (a carbonyl compound). As will be explained in greater detail below, it has been discovered that carbonyl compounds can be produced with high selectivity by contacting a compound comprising a secondary hydroxyl group with a basic metal oxide catalyst at a temperature sufficient to maintain the compound comprising a secondary hydroxyl group in a vapor phase. The reaction temperature should be kept below the degradation temperature of the compound comprising a secondary hydroxyl group and below the degradation temperature of the catalyst. For example, when the compound comprising a secondary hydroxyl group is benzyl alcohol a temperature of 300° C. to 600° C. can be employed, or, more specifically, a temperature of 350° C. to 450° C. Surprisingly, the compound comprising a secondary hydroxyl group can be converted to a carbonyl compound in the absence of a hydrogen acceptor compound such as propionaldehyde.

Compounds comprising a secondary hydroxyl group broadly describes a class of compounds having the formula I:

(I)

wherein $R^1$ can be a hydrogen or an alkyl group having 1 to 20 carbons. $R^2$ can be an alkyl having 1 to 20 carbons or an aromatic group having 6 to 20 carbons. The alkyl groups of $R^1$ or $R^2$ can be a straight chain, a branched chain or cyclic (monocyclic or polycyclic). The alkyl groups of $R^1$ and $R^2$ can be saturated or unsaturated. The alkyl groups of $R^1$ and $R^2$ can comprise an additional substituent as long as the substituent does not prevent the conversion of the hydroxyl group to a carbonyl. Exemplary substituents include halogen, alkoxy, amino, and cyano. The aromatic group can be a monocyclic or polycyclic aromatic group that can be unsubstituted or can be substituted with groups such as alkyl groups having five or less carbons, halogen, alkoxy, amino, cyano, and the like. In some embodiments $R^1$ and $R^2$ can, together, form a cyclic or polycyclic system.

In one embodiment the compound comprising a secondary hydroxyl group is a benzyl alcohol. Suitable benzyl alcohols include p-methylbenzyl alcohol, p-ethylbenzyl alcohol, o-methylbenzyl alcohol, p-isobutylbenzyl alcohol, p-chlorobenzyl alcohol, 2,4-dichlorobenzyl alcohol, o-bromobenzyl alcohol, p-methoxybenzyl alcohol, p-ethoxybenzyl alcohol, 2-ethynylbenzyl alcohol, 4-ethynylbenzyl alcohol, 2-amino-3-methylbenzyl alcohol, 3-amino-4-methylbenzyl alcohol, 3-amino-2-methylbenzyl alcohol, 2-amino-5-methylbenzyl alcohol, 1,2-benzenedimethanol, 1-phenyl-1,2-ethanediol, and the like, as well as combinations comprising at least one of the foregoing. In one embodiment the benzyl alcohol comprises the compound benzyl alcohol, $C_6H_5CH_2OH$.

In one embodiment, the compound comprising a secondary hydroxyl group comprises cyclohexanol or a substituted cyclohexanol. In another embodiment the compound comprising a secondary hydroxyl group has the formula

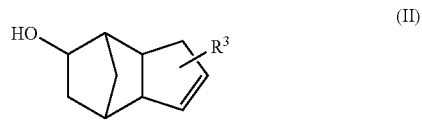

(II)

wherein $R^3$ is a hydrogen, an alkyl group having 1 to 5 carbons, a halogen, an alkoxy, an amino, or a cyano group.

Additionally it is contemplated that the compound comprising a secondary hydroxyl group may comprise more than one hydroxyl group. Importantly however, a hydroxyl group attached directly to an aromatic moiety (such as phenol) will not be converted to a carbonyl as that would require disruption of the aromatic system.

The amount of the compounds comprising a secondary hydroxyl group in relation to the amount of catalyst can be 0.5 to 2.5 WHSV (expressed in terms of grams of feed per gram of catalyst per hour). Within this range the amount can be greater than or equal to 1. Also within this range the amount can be less than or equal to 2.

The catalyst employed in the method includes, as a main constituent, at least one basic metal oxide. Suitable metals for the basic metal oxide, include iron, magnesium, calcium, barium, and strontium. The basic metal oxide can be obtained from a basic metal oxide precursor comprising a magnesium reagent, an iron reagent, or combinations comprising at least one of the foregoing. Any magnesium reagent that yields magnesium oxide can be used. Likewise, any iron reagent that yields iron oxide can be used.

Suitable magnesium reagents include, but are not limited to, magnesium oxide, magnesium hydroxide, magnesium carbonate, magnesium, basic magnesium carbonate, and mixtures comprising at least one of the foregoing. The magnesium reagent is generally in the form of a powder. For example, the magnesium reagents have an average particle size (as determined by measuring across the major diameter (i.e., the longest diameter) of each particle) of 5 micrometers to 50 micrometers, particularly 10 micrometers to 30 micrometers.

Examples of iron reagents used for the preparation of the catalyst include, but are not limited to, ferric nitrate, ferric sulfate, ferric chloride, ferrous nitrate, ferrous sulfate, and ferrous chloride. In one embodiment the iron reagent comprises ferric nitrate. The iron oxides can be in any form. For example, suitable forms of iron oxides include, but are not limited to, $FeO$, $Fe_2O_3$, $Fe_3O_4$, and mixtures comprising at least one of the foregoing.

The catalyst is formed by dry-blending the basic metal oxide precursor with at least one filler, and an optional pore former. As used in this disclosure, the term "dry blending" refers to the general technique in which the individual ingredients are initially mixed together in the dry state, without resorting to any "wet" techniques, such as suspension blending or precipitation. Any type of mechanical mixer or blender can be used, such as a ribbon blender. The term "filler" is inclusive of, but not limited to, lubricants, binders, and fillers.

The total amount of filler present in the catalyst composition can be less than or equal to 20% by weight, based on the total weight of filler and basic metal oxide precursor. In some embodiments, the total amount of filler is less than or equal to 10% by weight. Examples of fillers used in the catalyst composition include graphite and polyphenylene ether (PPE). In some embodiments the polyphenylene ether is used in an amount of less than or equal to 10% by weight, based on the total weight of the fillers and basic metal oxide precursor. In some embodiments the graphite is employed in an amount less than or equal to 5% by weight.

The optional pore former is a substance capable of aiding the formation of pores in the catalyst. For example, suitable pore formers include, but are not limited to waxes and polysaccharides. The waxes can include paraffin wax, polyethylene wax, microcrystalline wax, montan wax, and the like, as well as combination comprising at least one of the foregoing. The polysaccharide can include cellulose, carboxylmethyl cellulose, cellulose acetate, starch, walnut powder, citric acid, polyethylene glycol, oxalic acid, stearic acid, and the like, as well as combinations comprising at least one of the foregoing. Also useful are anionic and cationic surfactants, generally long chain ($C_{10-28}$) hydrocarbons containing neutralized acid species (e.g., carboxylic acid, phosphoric acid, and sulfonic acid species).

The optional pore former is employed in an amount sufficient to provide an average pore diameter of 50 angstroms to 300 angstroms after calcination, or, more specifically, 100 angstroms to 300 angstroms after calcination. For example, the pore former can be present in an amount of 0.5 wt. % to 50 wt. %, based on a total weight of basic metal oxide precursor, filler, and pore former. Within this range, the pore former can be present in an amount less than or equal to 40 wt. %, or, more specifically, less than or equal to 30 wt. %. Also within this range, the pore former can be present in amount greater than or equal to 2 wt. %, or, more specifically, greater than or equal to 5 wt. %.

In some embodiments, the catalyst has a bimodal distribution of pores. Without wanting to be bound by theory, it is believed that the first and smaller diameter pore distribution is obtained from the basic metal oxide precursor during the calcination process, i.e. these pores are of similar dimension to those obtained from calcination of the basic metal oxide precursor not containing the pore former. The second and larger diameter pore distribution is believed to be the result of the addition and calcination of the pore former reagent itself, i.e. these pore diameters would not be found in substantial quantities after calcination of a basic metal oxide precursor not containing the pore former.

In one embodiment, the bimodal distribution of pores has a first distribution of pores in which the first distribution has an average pore diameter less than 100 angstroms and a second distribution of pores in which the second distribution has an average diameter greater than or equal to 100 angstroms and less than or equal to 500 angstroms.

After dry-blending of the basic metal oxide precursor, filler (or multiple fillers) and optional pore former is complete, the blended, solid catalyst composition is in the form of a powder. The powder usually has a bulk density of 0.1 grams per cubic centimeter ($g/cm^3$) to 0.5 $g/cm^3$, or, more specifically, 0.25 $g/cm^3$ to 0.5 $g/cm^3$. The powder then generally undergoes further processing prior to being shaped into a desired form. For example, the power can be sieved (to obtain a more narrow particle distribution), milled, compressed, and the like. In most embodiments, the catalyst composition is deaerated after dry-blending, and prior to additional processing. Deaeration further increases the bulk density of the material by forcibly removing entrained gas (primarily air) from within the powder.

The catalyst can be formed into any desired shape. For example, the catalyst may be compressed into a pellet or "tablet", which can be accomplished by pelletizing equipment, including, but not limited to that equipment described in U.S. Pat. No. 4,900,708. The shaped catalyst composition is then calcined. Calcination is usually carried out by heating the catalyst at a temperature sufficient to convert the basic metal oxide precursor to basic metal oxide, which is the active species in the catalyst. Calcination increases the surface area of the catalyst. The calcination temperature can vary depending on the metal precursor, but is generally 350° C. to 600° C. The calcination atmosphere can be oxidizing, inert, or reducing. Alternatively, the catalyst can be calcined at the beginning of the benzylation reaction. In other words, calcination can take place in the presence of the feed materials, e.g., phenol and benzyl alcohol.

The surface area of the catalyst pellets can be 50 square meters per gram ($m^2/g$) to 300 $m^2/g$, or, more specifically, 120 square meters per gram ($m^2/g$) to 200 $m^2/g$, based on BET (Brunauer, Emmett, and Teller) analysis. The uncalcined pellets have pellet density of 1.3 $g/cm^3$ to 2.1 $g/cm^3$. Within this range, the pellets have a pellet density of greater than or equal to 1.4 $g/cm^3$, particularly greater than or equal to 1.6 $g/cm^3$. Also within this range, the pellets have a pellet density of less than or equal to 2.0 $g/cm^3$, particularly less than or equal to 1.9 $g/cm^3$.

In one embodiment, the catalyst pellets have a surface area to volume ratio of 950 square meters per cubic meter ($m^2/m^3$) to 4000 $m^2/m^3$. Within this range, the catalyst pellets particularly have a surface area to volume ratio greater than or equal to 1100 $m^2/m^3$ and more particularly greater than or equal to 1300 $m^2/m^3$. Also within this range, the catalyst pellets have a surface area to volume ratio less than or equal to 3800 $m^2/m^3$ and more particularly less than or equal to 3000 $m^2/m^3$.

In another embodiment, the catalyst pellets have an aspect ratio of 0.7 to 1.0. Within this range, the aspect ratio is particularly greater than or equal to 0.72 and more particularly greater than or equal to 0.75. Also within this range, the aspect ratio is particularly less than or equal to 0.95 and more particularly less than or equal to 0.90. Aspect ratio is herein defined as the ratio of length to diameter or length to width.

In operation, the compound comprising a secondary alcohol is introduced into a vessel containing the catalyst (herein after "catalyst bed" for ease in discussion). The temperature of the catalyst bed is maintained at a temperature sufficient to maintain the reactant in a vapor phase (e.g., a temperature of 300° C. to 600° C.). The reaction proceeds at atmospheric pressure, but pressures above or below can also be used. This reaction can also be carried out in the presence of water vapor. For example, the water vapor can be present in an amount of 1 wt. % to 35 wt. %, based on a total weight of the reactants, or, more specifically, 5 wt. % to 25 weight %.

The method allows for a selectivity of greater than or equal to 90% of the corresponding carbonyl product, or, more specifically, a selectivity of greater than or equal to 95%. Stated another way, embodiments are disclosed where essentially no byproducts are produced. For example, less than or equal to 1 wt. % of the total weight of the reaction products are byproducts.

The following examples are provided merely for illustration and representation of an example of making carbonyl compounds, and should not be considered as limiting the scope of this disclosure.

EXAMPLES

Example 1

Approximately 10 grams of magnesium carbonate were mixed with 1 gram of wax using a high-speed sheer blender for 10 minutes. The blending process was carried out under liquid nitrogen to allow homogenous mixing. The resulting blend was formed into pellets and calcined at temperatures varying from 390° C. to 410° C., using a ramp rate of 0.2 degrees Celsius per minute (° C./min) to 5° C./min under nitrogen. The nitrogen flow was maintained at 0.06 grams of nitrogen per hour per gram (g/hr/g) to 10 g/hr/g of catalyst. The starting temperatures of calcination were also varied from room temperature to 200° C. Approximately 300 milligrams of calcined sample was subjected to surface area and porosity measurement using a Micromeritics 2010 analyzer. The pore size distribution and surface area were obtained from the nitrogen desorption isotherm. The overall average pore diameter was 120 angstroms to 180 angstroms. The pore volume was 0.5 cubic centimeters per gram (cc/g) to 0.7 cc/g. The surface area was 100 $m^2/g$ to 250 $m^2/g$.

Example 2

A packed bed reactor was loaded with 5 cubic centimeters (cc) of magnesium carbonate pellets, having an average particle size of 1000 micrometers to 1400 micrometers. This catalyst was calcined in-situ for 16 to 22 hours at 390° C. at a rate of 0.2 to 5° C./min under 0.06 to 0.24 (10) g of nitrogen/hr/g of catalyst. The reaction was performed under atmospheric pressure. After calcination, the temperature was increased from 390° C. to 475° C. within two hours under nitrogen atmosphere. Once the reaction temperature was reached the nitrogen was turned off and the nitrogen was flushed out of the reactor. After 15 minutes of attaining this temperature, benzyl alcohol was introduced at 0.12 cc/min. The oxidation reaction was carried out under isothermal condition for a period of 16 hours. The constitution of the reaction mixture was monitored by gas chromatography/mass spectrometry. The results at the end of 16 hours are shown in Table 1.

TABLE 1

| Products | Yield |
| --- | --- |
| Benzaldehyde | 36.67 |
| Benzyl alcohol | 62.94 |
| Other | 0.38 |

This example illustrates that essentially the only product produced by the reaction is benzaldehyde. The other products constituted only 1% of the products, resulting in a 99% selectivity for benzaldehyde.

Example 3

The procedure described in Example 2 was used but substituting a compound having the formula III (referred to a TCD alcohol in the table) for the benzyl alcohol.

The reaction was run for 2 hours and produced the corresponding saturated and unsaturated ketone. The result is shown below in Table 2.

TABLE 2

| Products | Yield |
| --- | --- |
| TCD alcohol | 4 |
| TCD ketone-Saturated | 5 |
| TCD ketone-Unsaturated | 64.5 |
| Other products | 26.5 |

As can be seen from the foregoing examples the method allows for a relatively low cost catalyst to be employed, while allowing for high selectivity for the carbonyl product. Accordingly, a reduction in separation costs can be realized. Further, this method allows for a continuous method to be employed, which can increase production compared to batch methods.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the invention scope thereof. It is, therefore intended that the invention not be limited to the particular embodiment disclosed as the best mode contemplated for carrying out this invention, but that the invention will include all embodiments falling within the scope of appended claims.

What is claimed is:

1. A method of making a carbonyl compound comprising contacting a compound comprising a secondary hydroxyl group with a basic metal oxide catalyst at a temperature sufficient to maintain the compound comprising a secondary hydroxyl group in a vapor phase wherein the basic metal oxide catalyst consists essentially of a basic metal oxide and further wherein the compound comprising a secondary hydroxyl group has the formula

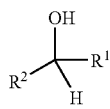
(I)

wherein $R^1$ is a hydrogen or an alkyl group having 1 to 20 carbons and $R^2$ is an aromatic group having 6 to 20 carbons or the compound comprising a secondary hydroxyl group is a cyclohexanol or substituted cyclohexanol.

2. The method of claim 1, wherein the temperature is 300° C. to 600° C.

3. The method of claim 1 wherein $R^2$ is a monocyclic or polycyclic aromatic group.

4. The method of claim 1 wherein $R^1$ and $R^2$ together form a polycyclic system.

5. The method of claim 1, wherein the compound comprising a secondary hydroxyl group is a benzyl alcohol selected from the group consisting of benzyl alcohol, p-methylbenzyl alcohol, p-ethylbenzyl alcohol, o-methylbenzyl alcohol, p-isobutylbenzyl alcohol, p-chlorobenzyl alcohol, 2,4-dichlorobenzyl alcohol, o-bromobenzyl alcohol, p-methoxybenzyl alcohol, p-ethoxybenzyl alcohol, and combinations comprising at least one of the foregoing.

6. The method of claim 1 wherein the compound comprising a secondary hydroxyl group is cyclohexanol.

7. The method of claim 1 wherein the compound comprising a secondary hydroxyl group has the formula

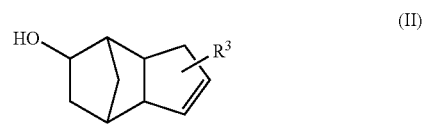
(II)

wherein $R^3$ is a hydrogen, an alkyl group having 1 to 5 carbons, a halogen, an alkoxy, an amino, or a cyano group.

8. The method of claim 1, wherein the basic metal oxide catalyst is obtained from a basic metal oxide precursor comprising a magnesium reagent.

9. The method of claim 1, wherein the basic metal oxide catalyst comprises a bimodal pore distribution.

10. The method of claim 9, wherein the bimodal pore distribution comprises a first distribution of pores having an average pore diameter less than 100 angstroms and a second distribution of pores having an average diameter greater than or equal to 100 angstroms and less than or equal to 500 angstroms.

11. The method of claim 1, wherein the basic metal oxide catalyst comprises an average pore diameter of 50 angstroms to 300 angstroms.

12. The method of claim 1, wherein the basic metal oxide catalyst has a surface area of 50 m²/g to 300 m²/g, based on BET analysis.

13. The method of claim 1, wherein method has a selectivity of greater than or equal to 95%.

* * * * *